United States Patent
Aloe et al.

(10) Patent No.: US 10,145,980 B2
(45) Date of Patent: Dec. 4, 2018

(54) WRIST-DETECTION ALGORITHM

(71) Applicant: Apple Inc., Cupertino, CA (US)

(72) Inventors: Robert T. Aloe, San Jose, CA (US); Sankalita Saha, Redwood City, CA (US); Stephen J. Waydo, Campbell, CA (US); Daniel J. Culbert, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/703,889

(22) Filed: Sep. 13, 2017

(65) Prior Publication Data
US 2018/0003855 A1    Jan. 4, 2018

Related U.S. Application Data

(63) Continuation of application No. 14/845,156, filed on Sep. 3, 2015, now Pat. No. 9,766,370.

(Continued)

(51) Int. Cl.
*G01J 1/16*    (2006.01)
*G01V 8/12*    (2006.01)
(Continued)

(52) U.S. Cl.
CPC .............. *G01V 8/12* (2013.01); *A61B 5/0059* (2013.01); *A61B 5/11* (2013.01); *A61B 5/681* (2013.01);
(Continued)

(58) Field of Classification Search
CPC ........ G01V 8/12; A61B 5/681; A61B 5/0059; A61B 5/6844; A61B 5/11; A61B 2562/0219
(Continued)

(56) References Cited

U.S. PATENT DOCUMENTS 5,483,261 A    1/1996    Yasutake
5,488,204 A    1/1996    Mead et al.
(Continued)

FOREIGN PATENT DOCUMENTS

JP    2000-163031 A    6/2000
JP    2002-342033 A    11/2002

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

(Continued)

*Primary Examiner* — Seung C Sohn
(74) *Attorney, Agent, or Firm* — Morrison & Foerster LLP

(57) ABSTRACT

Algorithms for detecting whether a device is properly secured to a user's skin are described. The operation of a device, such as a wearable device, can be adjusted based on whether the device is properly secured to a user's skin (e.g., on-wrist) or not properly secured to the user's skin (e.g., off-wrist). For example, certain functions can be disabled for power-saving, security or other purposes if the device is off-wrist. In order to avoid falsely identifying the device as off-wrist or on-wrist, algorithms for detecting whether the device is on-wrist or off-wrist can calculate one or more variances based on signals measured by a light sensor and compare the one or more variances with one or more thresholds. Comparing the one or more variances to the one or more threshold can improve the accuracy of wrist-detection algorithms.

20 Claims, 12 Drawing Sheets

Related U.S. Application Data

(60) Provisional application No. 62/163,304, filed on May 18, 2015.

(51) Int. Cl.
*A61B 5/00* (2006.01)
*A61B 5/11* (2006.01)

(52) U.S. Cl.
CPC .... *A61B 5/6844* (2013.01); *A61B 2562/0219* (2013.01)

(58) Field of Classification Search
USPC ...................................................... 250/206.1
See application file for complete search history.

(56) References Cited

U.S. PATENT DOCUMENTS

| | | | |
|---|---|---|---|
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |
| 6,771,994 B2 | 8/2004 | Kiani et al. | |
| 6,794,194 B2 | 9/2004 | Fava et al. | |
| 7,015,894 B2 | 3/2006 | Morohoshi | |
| 7,184,064 B2 | 2/2007 | Zimmerman et al. | |
| 7,663,607 B2 | 2/2010 | Hotelling et al. | |
| 7,983,851 B2 | 7/2011 | Jensen | |
| 8,280,469 B2 | 10/2012 | Baker, Jr. | |
| 8,356,594 B2 * | 1/2013 | Ujhazy | A61M 16/0051 128/204.18 |
| 8,479,122 B2 | 7/2013 | Hotelling et al. | |
| 8,532,728 B2 | 9/2013 | Diab et al. | |
| 9,547,792 B2 * | 1/2017 | Terada | G06F 3/005 |
| 2006/0197753 A1 | 9/2006 | Hotelling | |
| 2014/0364102 A1 | 12/2014 | Pham et al. | |

OTHER PUBLICATIONS

Notice of Allowance dated Jun. 1, 2017, for U.S. Appl. No. 14/845,156, filed Sep. 3, 2015, eight pages.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

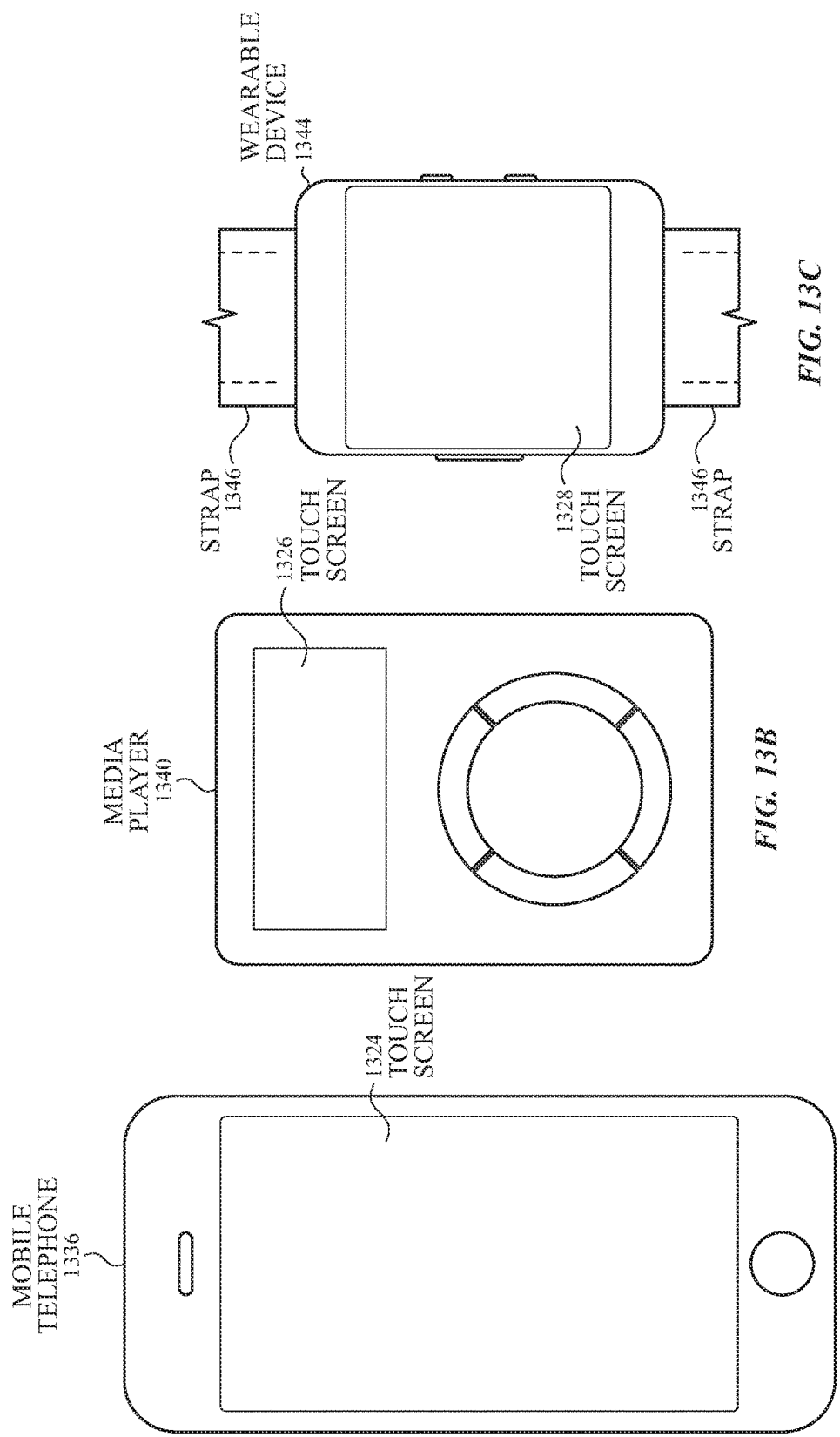

WRIST-DETECTION ALGORITHM

CROSS-REFERENCES TO RELATED APPLICATIONS

This application is a continuation of U.S. patent application Ser. No. 14/845,156 (now U.S. Publication No. 2016-0341600), filed on Sep. 3, 2015, which claims benefit of U.S. Provisional Patent Application No. 62/163,304, filed May 18, 2015, which is hereby incorporated by reference in their entirety.

FIELD OF THE DISCLOSURE

This relates generally to algorithms for detecting whether a device is properly secured to a user's skin, and more specifically to using variance checks to determine whether the device is properly secured to a user's skin.

BACKGROUND OF THE DISCLOSURE

A device, such as a wearable device, can include one or more light emitters and one or more light sensors. The one or more light emitters and one or more light sensors can be used to detect signals. For example, a photoplethysmogram (PPG) signal can be obtained by measuring the perfusion of blood within the skin of a user. The signals detected by the one or more light sensors can be used to detect whether the device is properly secured to a user's skin.

BRIEF SUMMARY OF THE DISCLOSURE

This relates to algorithms for detecting whether a device is properly secured to a user's skin. The operation of a device, such as a wearable device, can be adjusted based on whether the device is properly secured to a user's skin (e.g., on-wrist) or not properly secured to the user's skin (e.g., off-wrist). For example, certain functions can be disabled for power-saving, security or other purposes if the device is off-wrist. In order to avoid falsely identifying the device as off-wrist or on-wrist, algorithms for detecting whether the device is on-wrist or off-wrist can calculate one or more variances based on signals measured by a light sensor and compare the one or more variances with one or more thresholds. Comparing the one or more variances to the one or more thresholds can improve the accuracy of wrist-detection algorithms.

BRIEF DESCRIPTION OF THE DRAWINGS

FIGS. 13A-13C illustrate systems in which examples of the disclosure can be implemented.

DETAILED DESCRIPTION OF THE DISCLOSURE

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

This relates to algorithms for detecting whether a device is properly secured to a user's skin. The operation of a device, such as a wearable device, can be adjusted based on whether the device is properly secured to a user's skin (e.g., on-wrist) or not properly secured to the user's skin (e.g., off-wrist). For example, certain functions can be disabled for power-saving, security or other purposes if the device is off-wrist. In order to avoid falsely identifying the device as off-wrist or on-wrist, algorithms for detecting whether the device is on-wrist or off-wrist can calculate one or more variances based on signals measured by a light sensor and compare the one or more variances with one or more thresholds. Comparing the one or more variances to the one or more thresholds can improve the accuracy of wrist-detection algorithms.

Figure 1:
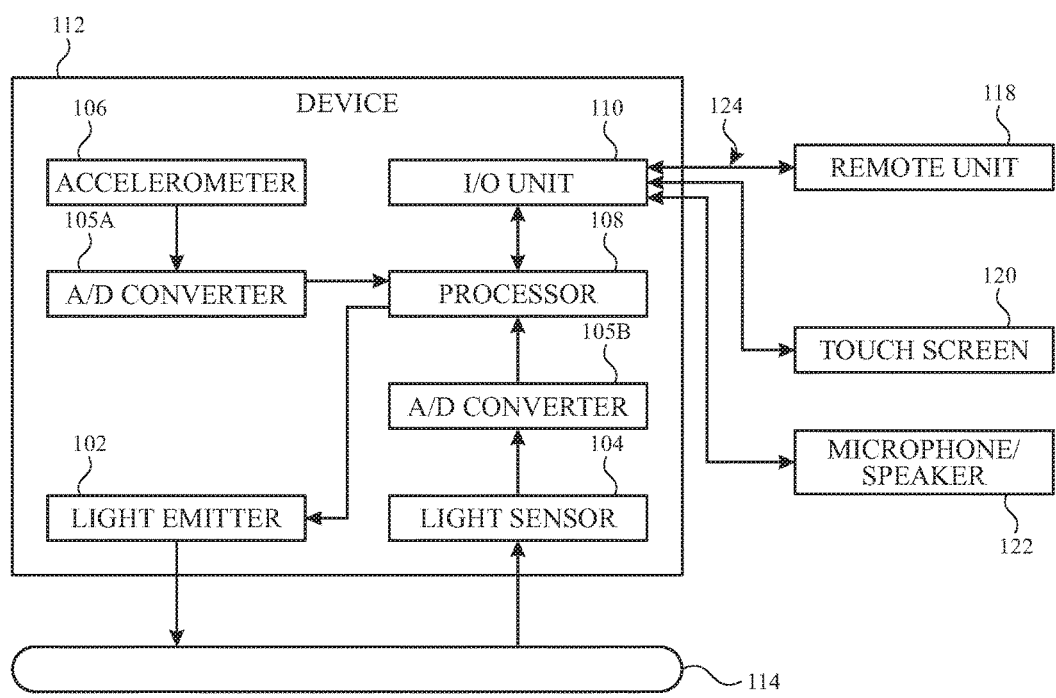
FIG. 1 illustrates a block diagram of an example system implementing a wrist-detection algorithm according to examples of the disclosure.

FIG. 1 illustrates a block diagram of an example system implementing a wrist-detection algorithm according to examples of the disclosure. As illustrated in FIG. 1, the block diagram can include a light emitter 102, light sensor 104, analog-to-digital converters (ADCs) 105a and 105b, accelerometer 106, processor 108 and input/output (I/O) unit 110. Although only a single processor 108 is shown, device 112 can include more than one processor or other processing circuitry. These components can be incorporated within a physical device 112 that can be worn or held by a user so as to secure the device to a user's skin (e.g., a user's wrist) or otherwise attached to an article of clothing worn by the user, with the light emitter 102 and light sensor 104 positioned proximate to a user's skin. Alternately, the device 112 can be entirely or partially incorporated within a smartphone or other portable device such that a user can hold the smartphone in a manner to cause the below-described light beam to be reflected from the user's skin back into a light sensor positioned within the smartphone itself. A portion of the light from light emitter 102 can be absorbed by the skin, vasculature, and/or blood, among other possibilities, and a portion can be reflected back to a light sensor 104 co-located with the light emitter. The signals from the light sensor 104 can include heart rate signals due to the blood pulse wave.

Although illustrated in FIG. 1 as having only a single channel formed by a single light emitter 102 and light sensor 104, in other examples multiple channels can be used in the system. The multiple channels can be created by increasing the number of emitter/sensor pairs, where each emitter/ sensor pair can create a new channel, for example. In other examples, multiple channels can be created using different light paths from one emitter to multiple sensors (e.g., one emitter and five sensors can produce five light paths). In yet other examples, multiple channels can be created using different light paths from multiple emitters to multiple sensors (e.g., two emitters and two sensors can produce four light paths including two paths from a first emitter to each of the two sensors and two paths from a second emitter to each of the two sensors). The one or more light emitters can produce light in ranges corresponding to infrared (IR), green, amber, blue and/or red light, among other possibilities. In some examples, a light emitter can be a light emitting diode (LED) and a light sensor can be a photodiode.

The accelerometer 106 can provide acceleration output signals indicative of acceleration due to movements of the user. For example, the device 112 can be worn on a user's wrist, and the accelerometer output signals can be indicative of the arm movements (e.g., arm swings, rotations, etc.) made by the user. In some examples, the accelerometer can be a three-axis accelerometer providing three-dimensional acceleration outputs (e.g., three channels of acceleration outputs). Additionally, device 112 can include a gyroscope (not shown) that can provide output signals indicative of the orientation of the device to the processor. The output signals from the accelerometer or gyroscope can also be used as inputs to wrist-detection algorithms.

In operation, the light emitter 102 can transmit a light beam to the user's skin 114, and the light beam can be reflected by the user's skin 114 and received by the light sensor 104. The light sensor 104 can convert this light into an electrical signal indicative of the intensity thereof. This electrical signal can be in analog form and can be converted into digital form by ADC 105b. The digital signal from the ADC 105b can be fed to the processor 108. Alternatively, the digital signal can be stored in a memory or a buffer external to processor 108. The outputs of the accelerometer 106 can also be converted to digital form using ADC 105a and either fed to processor 108 or alternatively stored in a memory or a buffer external to processor 108. The processor 108 can receive the digital signals from the light sensor 104 and the digital signals from the accelerometer 106, and can process these signals to determine whether device 112 is properly secured to a user's wrist ("on-wrist") or not properly secured to a user's wrist ("off-wrist").

The I/O unit 110 can take the form of one or more of a storage device, a visual display, an audible annunciator, a touch screen integrated with device 112, or other output indicator. The I/O unit 110 can, under program control from the processor 108, provide, for example, historical information in visual (e.g., numeric, tabular, graphic) or audible (e.g., synthesized voice or tone) form of a detected heart rate over a period of time. The I/O unit 110 can also provide, under control of the processor 108, average heart rate information or statistical information of the heart rate over a prior time period or periods. As a further example, the I/O unit 110 can provide current heart rate values as "real time" or instantaneous heart rate values displayed to the user periodically (e.g., every second) during the course of an ongoing exercise program.

The I/O unit 110 can be coupled to one or more of remote unit 118, touch screen 120 and microphone/speaker 122 or other device via wired or wireless communication links 124. The remote unit 118 can be a smart phone or other I/O device conveniently carried or worn by the user, or can be a distant computer or data server such as the user's home computer or the user's cloud storage service. The I/O unit 110 can receive input from the remote unit 118 or can receive input from the user by means of the touch screen 120 and/or the microphone/speaker 122. For example, I/O unit 110 can receive notifications from a remote unit 118 (e.g., a smartphone) that can be displayed on touch screen 120 when the device 112 is determined by processor 108 to be on-wrist. I/O unit 110 can also route audio information for phone calls between the remote unit 118 and the microphone/speaker 122 of device 112.

Detecting whether device 112 is properly secured to a user's wrist or not can be useful for optimizing operation of device 112. For example, applications requiring the device 112 be properly secured on a user's wrist can be disabled to save power when the device is determined to be off-wrist. Additionally or alternatively, when the device is off-wrist, the data from a sensor (e.g., light sensor 104) can be assumed to be compromised (i.e., bad or invalid) data when the device is determined to be off-wrist. For example, many health or fitness applications can be disabled when the device 112 is off-wrist, and/or data collected by sensors, such as heart rate data, that can be corrupted when the device is not properly secured to a user's body can be ignored or discarded. Likewise, when the device is off-wrist, one or more components of device 112 can be powered down (e.g., one or more processors can be powered down) for additional power savings. Additionally, when the device 112 is determined to be off-wrist, the device 112 can indicate to a remote device 118 not to send notifications or calls to the device 112 (and/or device 112 can be configured to not receive or operate in response to said notifications or calls). Similarly, determining that the device 112 is off-wrist can cause the device 112 to require a password to prevent access to the device 112 as a security feature.

Figure 2:
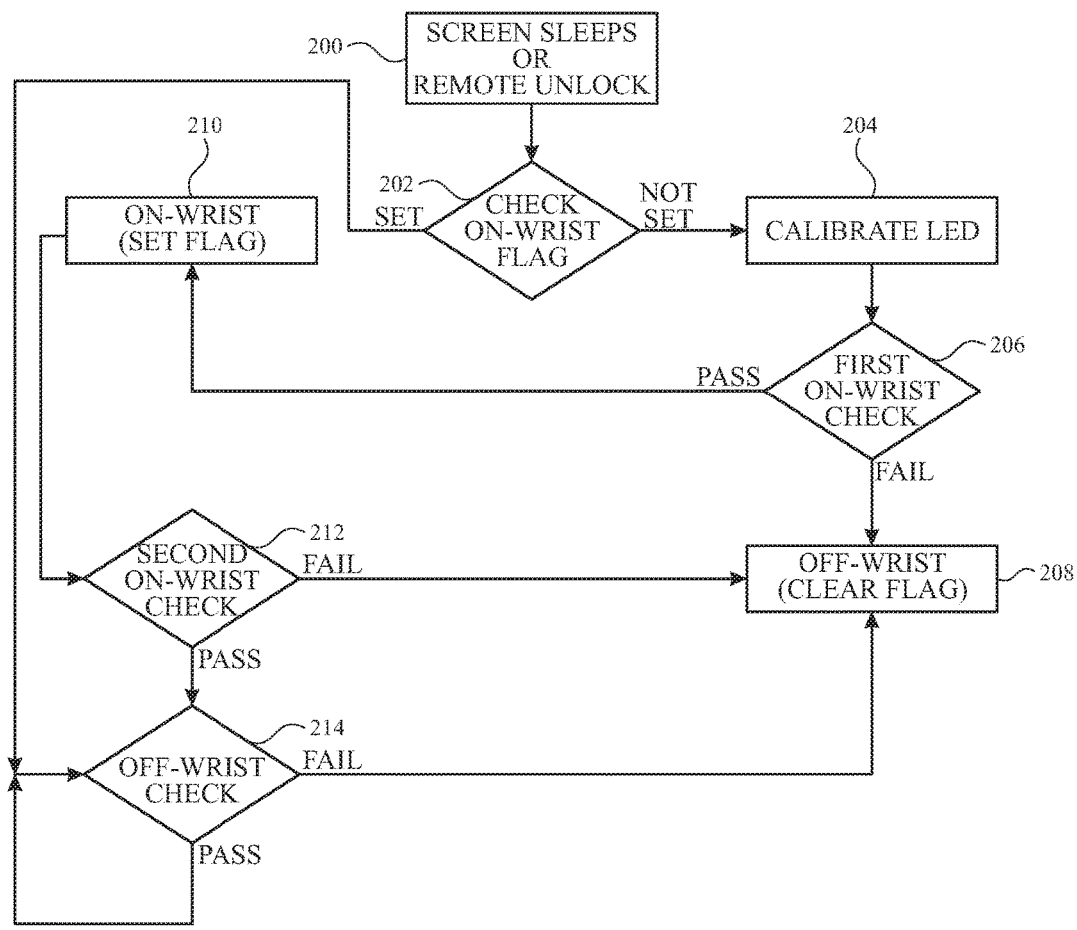
FIG. 2 illustrates an example high-level algorithm for performing wrist detection according to examples of the disclosure.

FIG. 2 illustrates an example high-level algorithm for performing wrist detection according to examples of the disclosure. The system (e.g., processor 108) can detect that the touch screen 120 of device 112 has been put to sleep or that a request from a remote unit (e.g., a smartphone) to remotely unlock device 112 has been received (200). In response to detecting that the touch screen has been put to sleep or that a remote unlock request has been received, the system can check the on-wrist/off-wrist state of the device (202). For example, the system can include a flag indicative of the state of the device, and the flag can either be set when the device is determined to be on-wrist or cleared when the device is determined to be off-wrist. When the system previously determined that the device was off-wrist (e.g., on-wrist flag cleared), the system can calibrate the light sensor 104 (e.g., an IR LED and photodetector pair) for proper operation (204). The calibration of the light sensor will be described in more detail below. After calibration, the system can perform a first on-wrist check, described in more detail below, to determine if the device is on-wrist (206). If the first on-wrist check fails, indicative that the device is off-wrist, the flag can remain not set (208). If the first on-wrist check passes, indicative that the device is now on-wrist, the system can set the flag and report that the device is on-wrist (210). When the on-wrist flag is set at 210, the system can perform a second on-wrist check (212). The second on-wrist check can be the same as the first on-wrist check or can be different than the first on-wrist check. The second on-wrist check will be described in more detail below. If the second on-wrist check fails, indicative that the device is off-wrist, the system can clear the flag and report that the device is off-wrist (208). If the second on-wrist check passes, the flag remains set and the system can perform an off-wrist check (214). The off-wrist check will be described in more detail below. If the off-wrist check fails, the system can clear the flag and report that the device is off-wrist (208). If the off-wrist check passes, the system continues to perform the off-wrist check (214) until the off-wrist check fails.

When the system previously determined that the device was on-wrist (e.g., on-wrist flag set at 202) after detecting that the touch screen has been put to sleep or that a remote unlock request has been received, the system can keep the flag set. The system can then proceed to the off-wrist check at 214 without requiring the first on-wrist check or the second on-wrist checks.

It should be understood that representing the state of the device with a flag is only an example, and the state of the device can be represented in other forms. Additionally or alternatively, in some examples, the state of the flag can be reported to a processor or remote device via an interrupt signal. In some examples, the interrupt signal can be sent only when the state of the device changes (e.g., from off-wrist to on-wrist or from on-wrist to off-wrist). In other examples, however, the state of the device can be reported via an interrupt each time that state is confirmed, even when the state does not change.

Figure 3:
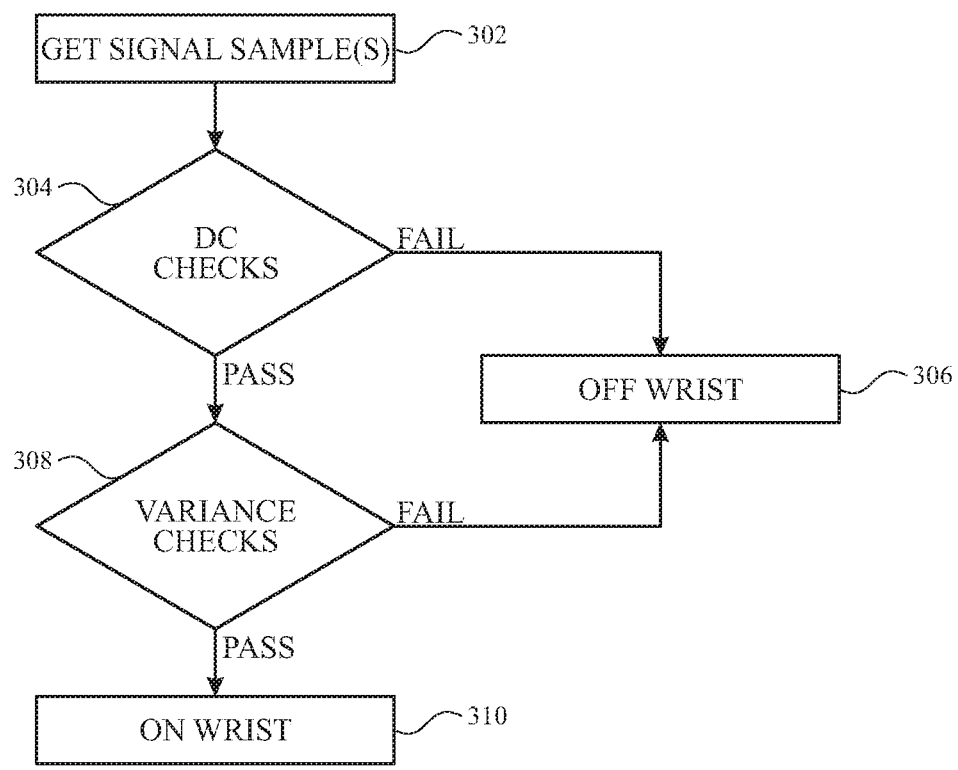
FIG. 3 illustrates an example high-level algorithm for performing an on-wrist check according to examples of the disclosure.

FIG. 3 illustrates an example high-level algorithm for performing an on-wrist check according to examples of the disclosure. The system can acquire signal samples from a sensor (302). In some examples, the sensor can be a photodetector. The photodetector can detect an intensity of light received when one or more light emitters (e.g., LEDs) are emitting light and can also detect the intensity of light received when the one or more light emitters are not emitting light. The signal associated with the measurement at the photodetector when the light emitter is active and emitting light can be represented as $LED_{ON}$, and the signal associated with the measurement at the photodetector when the light emitter is inactive and not emitting light can be represented as $LED_{OFF}$. The signal samples acquired at 302 can be the difference between the two measurements, $LED_{ON}$-$LED_{OFF}$, or alternatively can include $LED_{ON}$ and $LED_{OFF}$ separately. The system can perform direct current (DC) checks on the signal samples (304). The DC checks can include detecting that the signal sample meets or exceeds a threshold DC signal level. The DC checks can also include analyzing the DC signal level of the single sample and the intensity of the LED to determine if the values are within ranges associated with the device secured to human skin. For example, the DC checks can include calculating a ratio of the DC signal level to the intensity of the LED and determine if the ratio is within a range of values for a human. In some examples, the DC checks can be a two-step process, first checking the DC content of the signal sample and, assuming the DC content of the signal is sufficient, analyzing the ratio of the DC content of the signal sample to the LED intensity, though in other examples, these two checks can be in any order and independent of one another.

If the any of the DC checks fail (e.g., insufficient DC signal or ratio outside of a human range), the system can determine the state of the device to be off-wrist (e.g., clear the on-wrist flag or keep the flag not set) and, if applicable, report the off-wrist state (306). If the DC checks pass, the system can perform variance checks on the signal samples (308). The variance checks will be discussed in more detail below. If the variance checks fail, the system can determine the state of the device to be off-wrist (e.g., clear the on-wrist flag or keep the flag not set) and, if applicable, report the off-wrist state (306). If the variance checks pass, the system can determine the state of the device to be on-wrist (e.g., set the on-wrist flag or keep the flag set) and if applicable, report the on-wrist state (310).

Although not shown in the example of FIG. 3, the algorithm of FIG. 3 can also include additional checks such as a proximity check, saturation check, and/or a light emitter calibration check that will be described below.

Variance checks can helpful for properly identifying whether a device is properly secured to a user's wrist. Human skin can be modeled as a scattering volume. Light from an LED entering human skin can be reflected back to a photodetector and the signal received at the photodetector will change due to physical or physiological properties such as movement of the person, blood movement in the body, etc. When the device is on-wrist, the signal variance can be higher than when the device is off-wrist. The variance in the signal received at the photodetector can thereby be used to determine that the device is on-wrist. A threshold signal variance can be used to determine whether or not the signal sample variance corresponds to a device on-wrist or off-wrist. The threshold level can be set based on basic observations or experiments. In order to prevent falsely reporting that the device is off-wrist when the variance drops below the threshold signal variance for a short period of time, the system can require detecting low-variance (i.e., below the threshold) signal samples for a threshold period of time before determining and/or reporting the device to be off-wrist.

Figure 4:
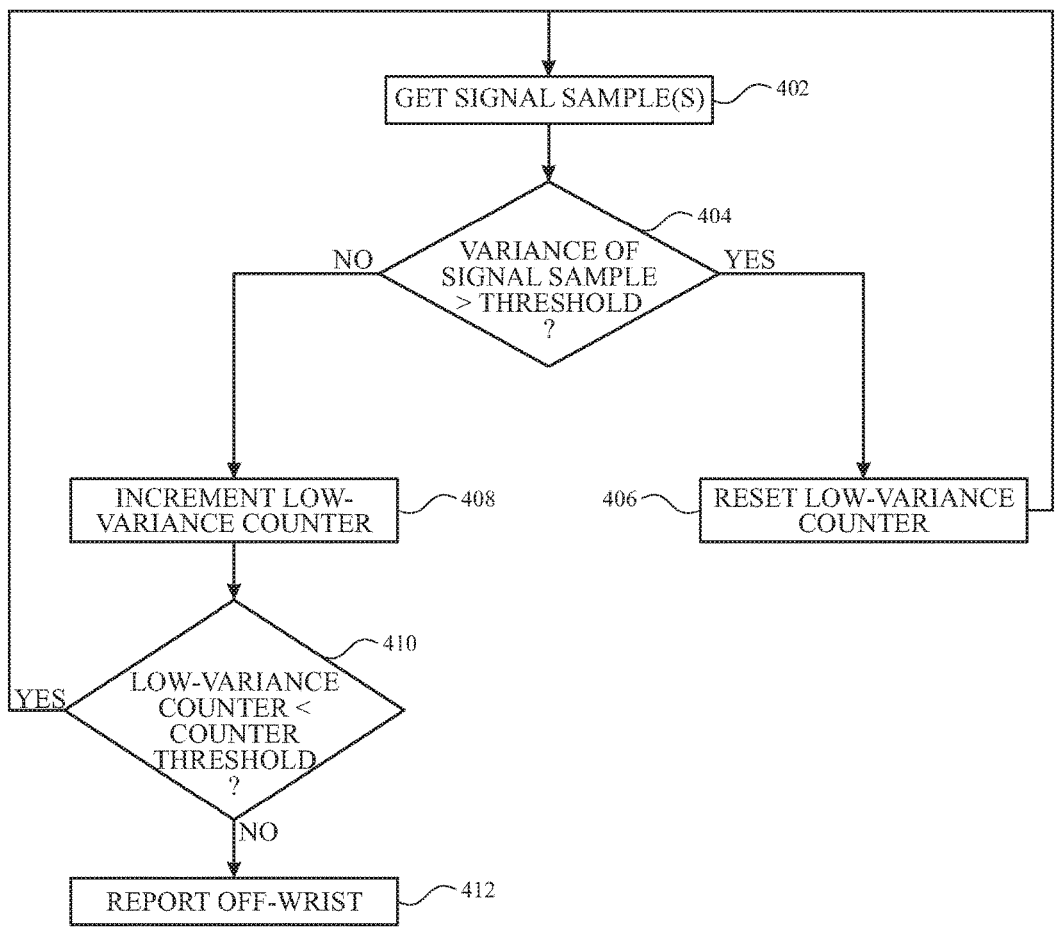
FIG. 4 illustrates an algorithm for performing variance checks according to examples of the disclosure.

FIG. 4 illustrates an algorithm for performing variance checks according to examples of the disclosure. The algorithm can begin by retrieving a signal sample (402). As discussed above, the signal sample can be a measurement of the difference between the signals received at a photodetector, i.e., $LED_{ON}$-$LED_{OFF}$. The system can calculate a variance of the signal sample ($VAR(LED_{ON}$-$LED_{OFF})$) and compare the variance to a threshold signal variance (404). If the variance meets or exceeds the threshold, corresponding to the device being on-wrist, the system can reset a counter that is keeping track of the number of low-variance signal samples (406). In other examples, rather than resetting the counter, the system can alternatively decrement the counter by one or more values. After resetting the low-variance counter, the system can get the next signal sample to perform the variance analysis on the next signal sample (402). If the result from calculating the variance of the signal sample is below the threshold signal variance, the system can increment the low-variance counter (408). The system can then compare the value of the low-variance counter to a counter threshold (410). The counter threshold can be set such that the number of low-variance signal samples corresponds to receiving low-variance signal samples for a threshold period of time. If the value of the low-variance counter is below the counter threshold, the system can get the next signal sample to perform the variance analysis on the next signal sample (402). If the value of the low-variance counter meets or exceeds the counter threshold, the system can determine and/or report the device is off-wrist, e.g., by clearing the on-wrist flag and/or generating an interrupt signal (412).

Although the example illustrated in FIG. 4 shows a counter that can be incremented or reset, it should be understood that the algorithm can be implemented differently so as not to rely on a counter. Similarly, the use of a counter in other figures of this description is likewise not to be interpreted to require a counter for implementation.

Figure 5:
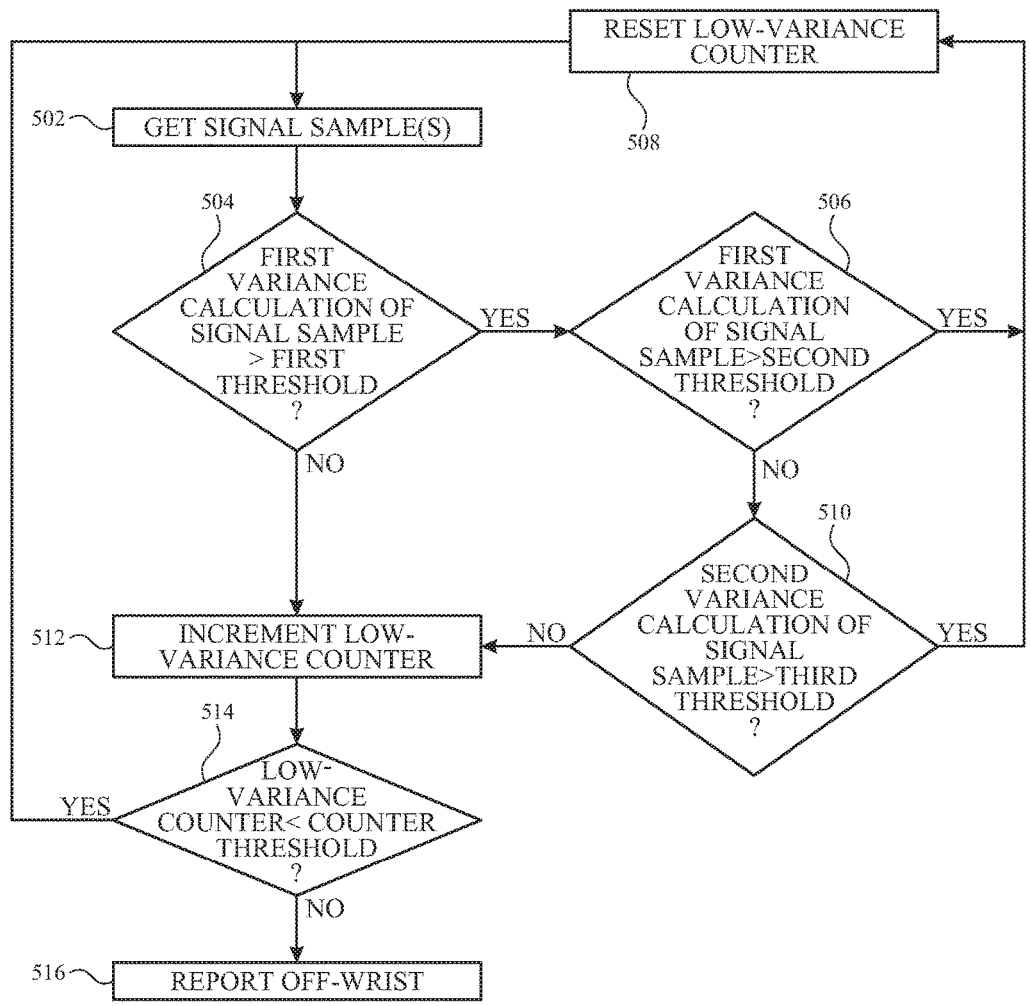
FIG. 5 illustrates another algorithm for performing variance checks according to examples of the disclosure.

In order to improve the performance of the variance checks, in some examples, a more robust algorithm can be implemented that includes additional variance checks and variance thresholds. A more robust algorithm can be used to reduce the number of false positives for detecting the device going off-wrist and also for falsely detecting the device staying on-wrist. FIG. 5 illustrates another algorithm for performing variance checks according to examples of the disclosure. Like the algorithm illustrated in FIG. 4, the algorithm illustrated in FIG. 5 can begin by retrieving a signal sample (i.e., $LED_{ON}$-$LED_{OFF}$) (502). The system can perform a first variance calculation of the signal sample (i.e., VAR($LED_{ON}$-$LED_{OFF}$)) and compare the result of the first variance calculation to a first threshold signal variance (504). If the result of the first variance calculation meets or exceeds the first threshold, corresponding to the device being likely on-wrist, the system can compare the result of the first variance calculation to a second threshold (506). The second variance threshold can be higher than the first variance threshold. If the result of the first variance calculation meets or exceeds the second threshold, corresponding to a very high variance, the system can reset (or decrement by one or more) a low-variance counter that is keeping track of the number of low-variance signal samples (508). After resetting the low-variance counter, the system can get the next signal sample to perform the variance analysis on the next signal sample (502).

If the first variance of the signal sample is below the second threshold, corresponding to an intermediate signal variance (i.e., between the first and second thresholds), the system can perform a second variance calculation for the signal sample, and compare the second variance calculation to a third variance threshold (510). The third threshold can be lower than the first and second thresholds. For example, the second variance calculation can include calculating the difference of the variance of the signal measured when the LED is on (VAR($LED_{ON}$)) and the variance of the signal measured when the LED is off (VAR($LED_{OFF}$)). In other words, the second variance calculation computes VAR($LED_{ON}$)−VAR($LED_{OFF}$). The result of the second variance calculation can be compared with the third variance threshold. If the result of the second variance calculation meets or exceeds the third variance threshold, the system can reset (or decrement by one or more) a low-variance counter that is keeping track of the number of low-variance signal samples (508). If the result of the second variance calculation is below the third variance threshold, the system can increment the low-variance counter (512). Alternatively, the system can also increment the low-variance counter when the result of the first variance calculation is below the first threshold (512).

After incrementing the low-variance counter, the system can then compare the value of the low-variance counter to a counter threshold (514). The counter threshold can be set such that the number of low-variance signal samples corresponds to receiving low-variance signal samples for a threshold period of time. If the value of the low-variance counter is below the counter threshold, the system can get the next signal sample to perform the variance analysis on the next signal sample (502). If the value of the low-variance counter meets or exceeds the counter threshold, the system can determine and/or that report the device is off-wrist, e.g., by clearing the on-wrist flag and/or generating an interrupt signal (516). Although the example illustrated in FIG. 5 shows a counter that can be incremented or reset, it should be understood that the algorithm can be implemented differently so as not to rely on a counter.

Figure 6:
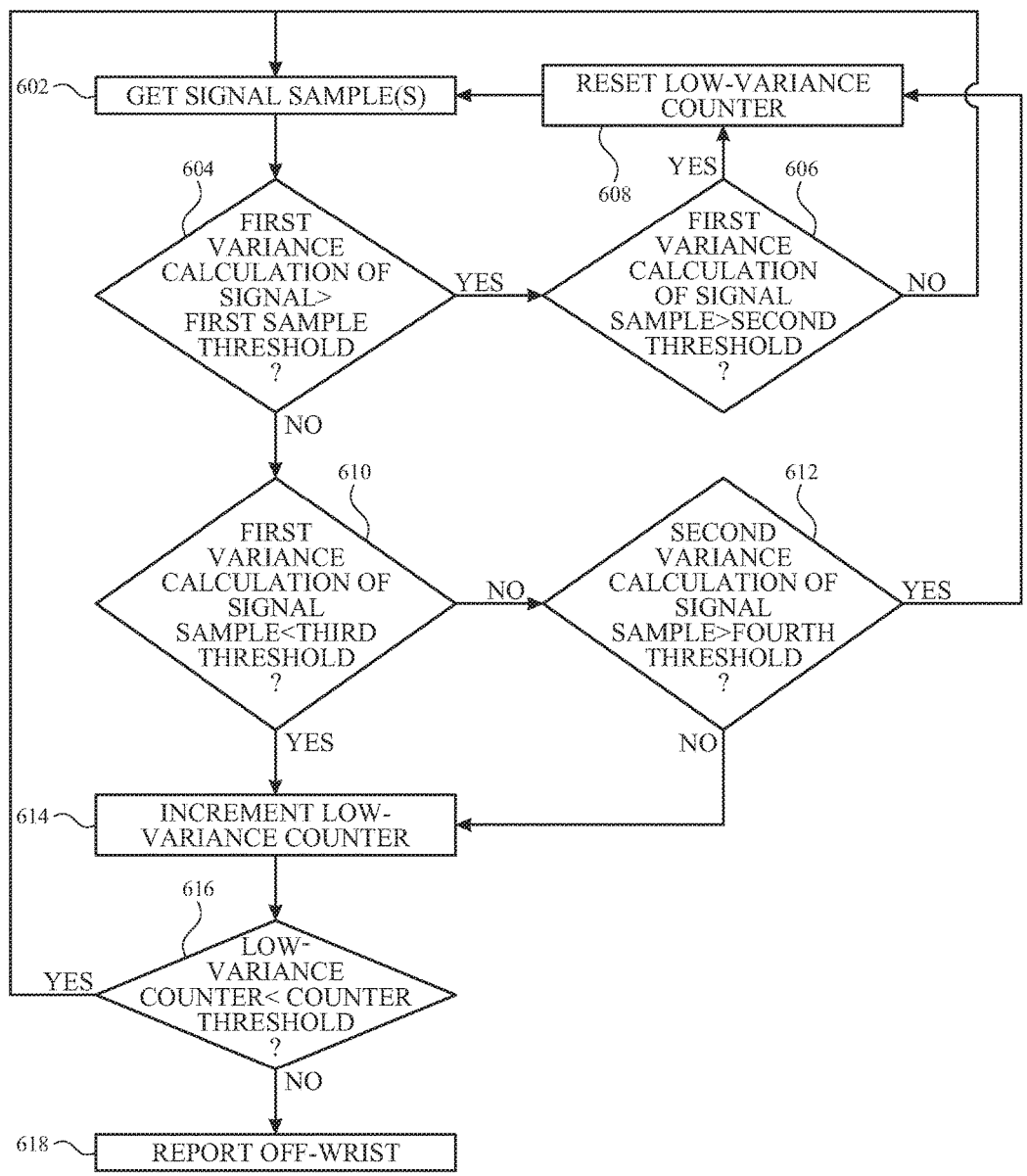
FIG. 6 illustrates another algorithm for performing variance checks according to examples of the disclosure.

FIG. 6 illustrates another algorithm for performing variance checks according to examples of the disclosure. Like the algorithm illustrated in FIG. 5, the algorithm illustrated in FIG. 6 can begin by retrieving a signal sample (i.e., $LED_{ON}$-$LED_{OFF}$) (602). The system can perform a first variance calculation of the signal sample (i.e., VAR($LED_{ON}$-$LED_{OFF}$)) and compare the result of the first variance calculation to a first threshold signal variance (604). If the result of the first variance calculation meets or exceeds the first threshold, the system can compare the result of the first variance calculation to a second threshold (606). The second variance threshold can be higher than the first variance threshold. If the result of the first variance calculation meets or exceeds the second threshold, corresponding to a very high variance, the system can reset (or decrement by one or more) a low-variance counter that is keeping track of the number of low-variance signal samples (608). After resetting the low-variance counter, the system can get the next signal sample to perform the variance analysis on the next signal sample (602). If the first variance of the signal sample is below the second threshold, the system can get the next signal sample to perform the variance analysis on the next signal sample without incrementing or resetting the counter (602).

If the result of the first variance calculation is below the first threshold, the system can compare the result of the first variance calculation to a third threshold (610). The third threshold can be lower than the first and second thresholds. If the result of the first variance calculation meets or exceeds the third threshold, the system can perform a second variance calculation for the signal sample, and compare the second variance calculation to a fourth variance threshold (612). For example, the second variance calculation can include calculating the difference of the variance of the signal measured when the LED is on (VAR($LED_{ON}$)) and the variance of the signal measured when the LED is off (VAR($LED_{OFF}$)). In other words, the second variance calculation computes VAR($LED_{ON}$)−VAR($LED_{OFF}$). The result of the second variance calculation can be compared with the fourth variance threshold. The fourth variance threshold can be lower than the first, second, and third thresholds. If the result of the second variance calculation meets or exceeds the fourth variance threshold, the system can reset (or decrement by one or more) a low-variance counter that is keeping track of the number of low-variance signal samples (608). If the result of the second variance calculation is below the fourth variance threshold, the system can increment the low-variance counter (614). Alternatively, the system can also increment the low-variance counter when the result of the first variance calculation is below the third threshold (614).

After incrementing the low-variance counter, the system can then compare the value of the low-variance counter to a counter threshold (616). The counter threshold can be set such that the number of low-variance signal samples corresponds to receiving low-variance signal samples for a threshold period of time. If the value of the low-variance counter is below the counter threshold, the system can get the next signal sample to perform the variance analysis on the next signal sample (602). If the value of the low-variance counter meets or exceeds the counter threshold, the system can determine and/or report that the device is off-wrist, e.g., by clearing the on-wrist flag and/or generating an interrupt signal (618). Although the example illustrated in FIG. 6 shows a counter that can be incremented or reset, it should be understood that the algorithm can be implemented differently so as not to rely on a counter.

In some examples, the first on-wrist check 206 can follow the algorithm of either FIG. 4 or FIG. 5, and the second on-wrist check 212 can follow the algorithm of FIG. 6, though in other examples, the first and second on-wrist checks can use different algorithms. The duration of the first on-wrist check and the second on-wrist check can also be the same in some examples, though in other examples the first on-wrist check can be a shorter duration check than the second on-wrist check. Alternatively, the duration of the second on-wrist check can be shorter than the first on-wrist check. Additionally or alternatively, the variance threshold levels and/or counter threshold levels can be the same or different between the algorithms of FIGS. 4-6.

Figure 7:
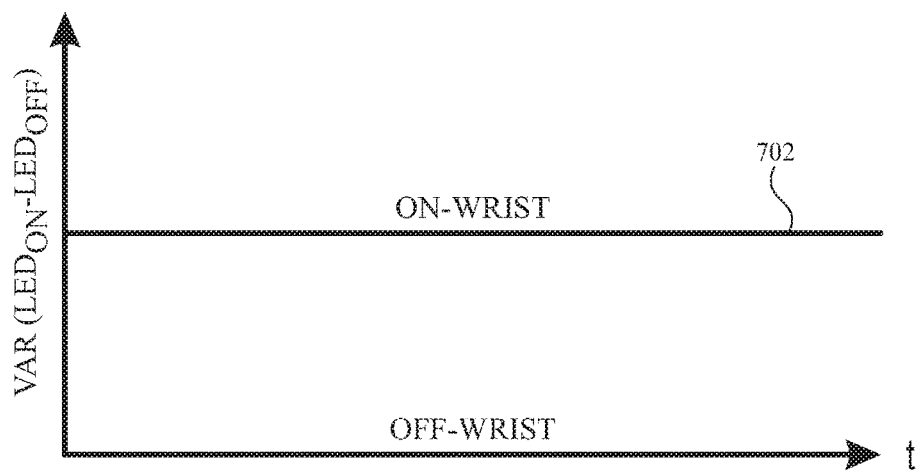
FIGS. 7-9B illustrate example variance threshold levels according to examples of the disclosure.

FIGS. 7-9B illustrate example variance threshold levels according to examples of the disclosure. For example, FIG. 7 illustrates an example variance threshold level that can correspond to the variance threshold level of the algorithm of FIG. 4. FIG. 7 shows a plot of the variance of the signal samples (i.e., VAR($LED_{ON}$-$LED_{OFF}$) versus time. The results of the variance calculation that meet or exceed variance threshold 702 can correspond to an on-wrist condition (i.e., where the low-variance counter can be reset or decremented). The results of the variance calculation that are below the variance threshold 702 can correspond to an off-wrist condition (i.e., where the low-variance counter can be incremented).

Figure 8A:
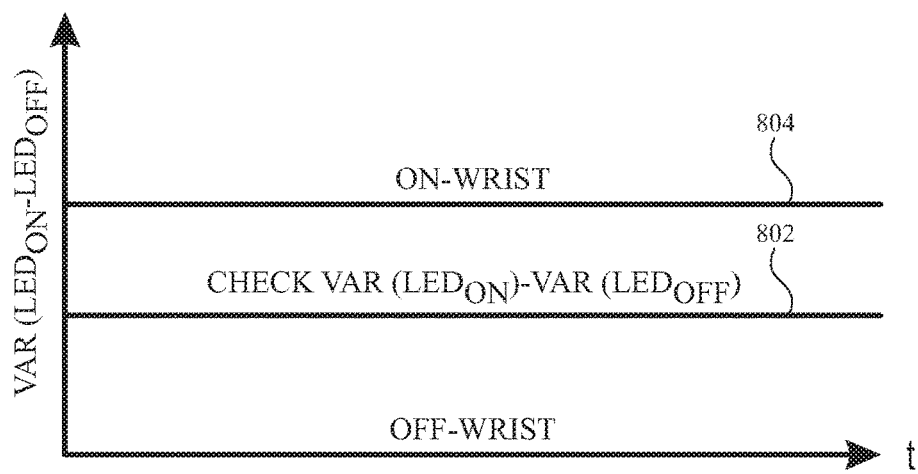

Similarly, FIG. 8A illustrates example variance threshold levels that can correspond to the first and second variance threshold levels of the algorithm of FIG. 5. Like FIG. 7, FIG. 8A illustrates a plot of the result of the first variance calculation of the signal samples (i.e., VAR($LED_{ON}$-$LED_{OFF}$) versus time. The results of the first variance calculation that are below first variance threshold 802 can correspond to an off-wrist condition (i.e., where the low-variance counter can be incremented). The results of the first variance calculation that meet or exceed both the first variance threshold 802 and the second variance threshold 804 can correspond to an on-wrist condition (i.e., where the low-variance counter can be reset or decremented). The results of the first variance calculation that meet or exceed the first variance threshold 802 but are below the second variance threshold 804 can correspond to signal samples that require the second variance calculation and threshold comparison described above with respect to FIG. 5 before making a determination about the condition of the device.

Figure 8B:
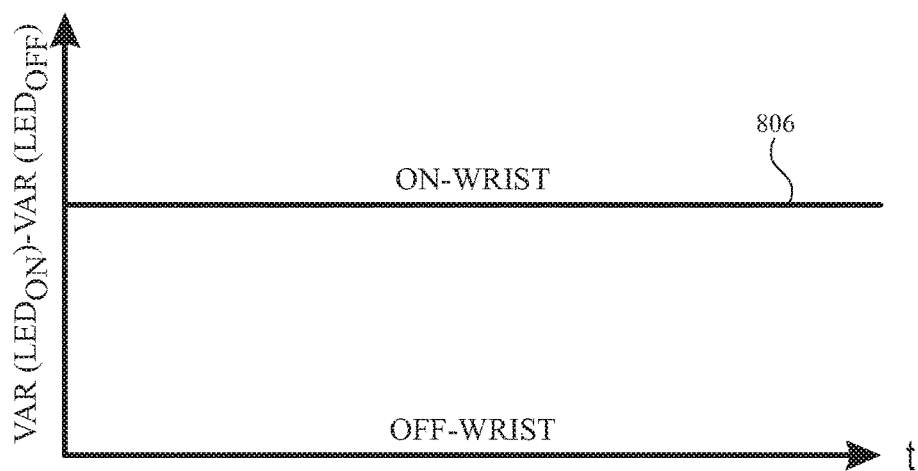

FIG. 8B illustrates a plot of the result of the second variance calculation of the signal samples (i.e., VAR($LED_{ON}$)–VAR($LED_{OFF}$)) versus time. The results of the second variance calculation that meet or exceed the third variance threshold 806 can correspond to an on-wrist condition (i.e., where the low-variance counter can be reset or decremented). The results of the variance calculation that are below the third variance threshold 806 can correspond to an off-wrist condition (i.e., where the low-variance counter can be incremented).

Figure 9A:
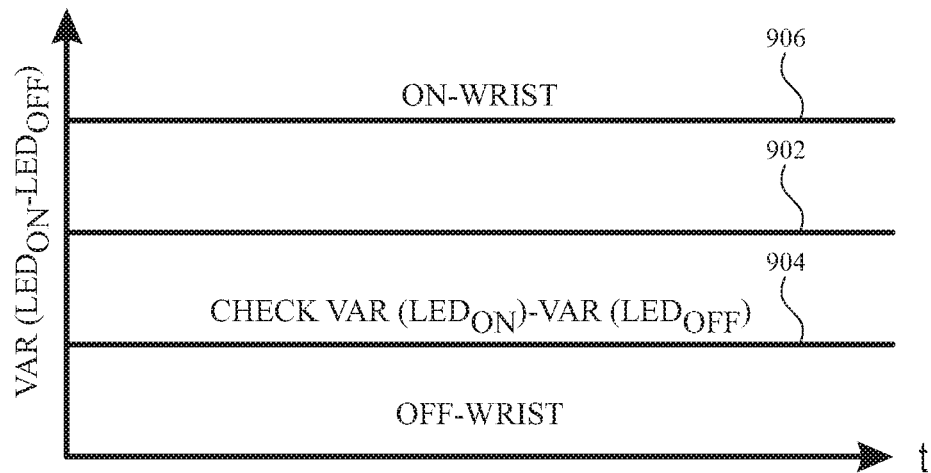

Likewise, FIG. 9A illustrates example variance threshold levels that can correspond to the first, second, and third variance threshold levels of the algorithm of FIG. 6. Like FIGS. 7 and 8A, FIG. 9A illustrates a plot of the result of the first variance calculation of the signal samples (i.e., VAR($LED_{ON}$-$LED_{OFF}$) versus time. The results of the first variance calculation that are below a first variance threshold 902 and a third variance threshold 904 can correspond to an off-wrist condition (i.e., where the low-variance counter can be incremented). The results of the first variance calculation that meet or exceed both the first variance threshold 902 and a second variance threshold 906 can correspond to an on-wrist condition (i.e., where the low-variance counter can be reset or decremented). The results of the first variance calculation that meet or exceed the first variance threshold 902 but are below the second variance threshold 906 can correspond to a condition where the counter is not incremented, decremented or reset. The results of the first variance calculation that are below the first variance threshold 902 but meet or exceed the third variance threshold 904 can correspond to signal samples that require the second variance calculation and threshold comparison described above with respect to FIG. 6 before making a determination about the condition of the device.

Figure 9B:
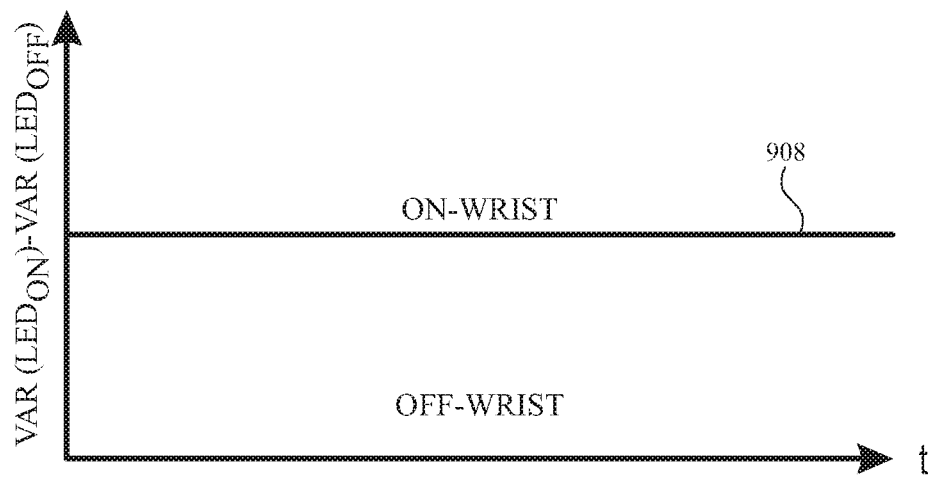

FIG. 9B illustrates a plot of the result of the second variance calculation of the signal samples (i.e., VAR ($LED_{ON}$)–VAR($LED_{OFF}$)) versus time. The results of the second variance calculation that meet or exceed the fourth variance threshold 908 can correspond to an on-wrist condition (i.e., where the low-variance counter can be reset or decremented). The results of the variance calculation that are below the fourth variance threshold 908 can correspond to an off-wrist condition (i.e., where the low-variance counter can be incremented).

Returning back to the algorithm of FIG. 2, the off-wrist check 214 can, in some examples, be implemented using the same variance check algorithms as the second on-wrist check 212. In some examples, the off-wrist check 214 can use different variance thresholds than used for the second on-wrist check 212. For example, the variance thresholds can be lowered for the off-wrist check so the device is less likely to falsely report an off-wrist condition.

Figure 10:
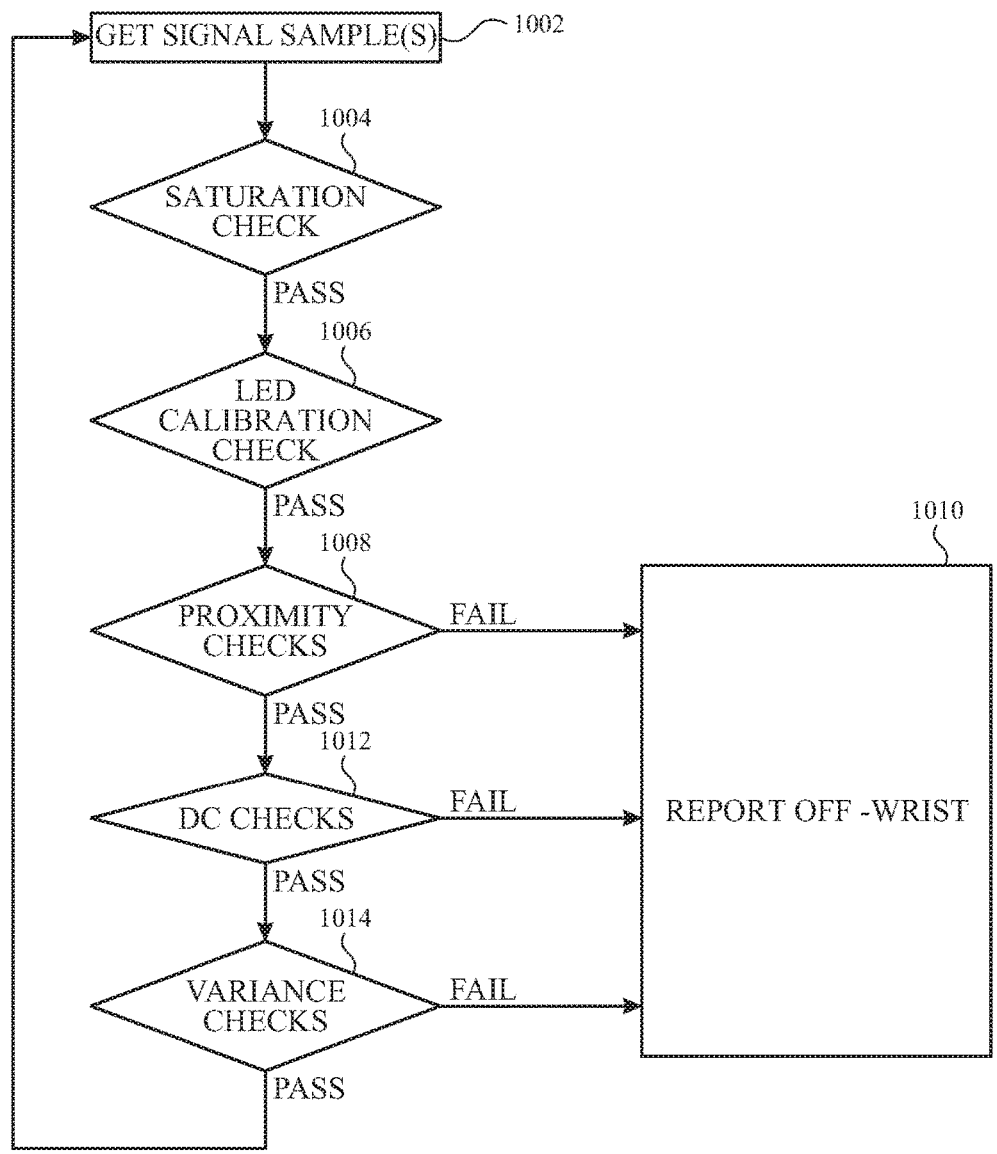
FIG. 10 illustrates an example high-level algorithm for performing an off-wrist check according to examples of the disclosure.

FIG. 10 illustrates an example high-level algorithm for performing an off-wrist check according to examples of the disclosure. The system can receive one or more signal samples, such as $LED_{ON}$-$LED_{OFF}$, for example (1002). The system can first perform a saturation check (1004) to determine whether the sensor (e.g., photodetector) is saturated by light from the ambient conditions and/or the light emitter (e.g., LED). The saturation check can, for example, first check for complete saturation due to ambient light. For example, if the signal level received by the photodetector is at 100% of the signal level permitted by the hardware when the LED is off (absolute saturation), the check can fail when the saturation persists for a first threshold period of time (e.g., 1-3 seconds). Such a case can correspond to ambient conditions that saturate the photodetector whether or not the LED is on, which can result in $LED_{ON}$-$LED_{OFF}$=0. When the saturation check fails under absolute saturation conditions, the system can determine and/or report that the device is off-wrist (1010). If the photodetector is not saturated when the LED is off, but is saturated when the LED is on, the saturation check will fail, but the result of the failed saturation test can depend on the degree of saturation of the photodetector when the LED is off. For example, when the photodetector is saturated more than a threshold amount of the photodetector signal range for a second threshold period of time, the saturation check can fail and the system can determine and/or report that the device is off-wrist (1010). The threshold amount can be 60%, for example, and more generally can be set in a range of 50-100% of the photodetector signal range. Alternatively, if the photodetector is not saturated more than the threshold amount for the second threshold period of time, the saturation test can still fail (because the photodetector is saturated when the LED is on), but the system can perform a recalibration of the LED and photodetector, and then rerun the saturation checks.

Recalibrating the LED and photodetector can include adjusting the intensity of the LED output such that the signal received by the photodetector is less than 50% of the photodetector signal range. In some examples, the intensity of the LED can be adjusted so that the received signal at the photodetector is between 20% and 50% of the photodetector signal range.

If the saturation check passes, the system can perform a calibration check for the light emitter and sensor (1006). The calibration check can, for example, check the signal level of the photodetector when the LED is on to determine if it is within a specific range. For example, the calibration check can determine whether the signal detected by the photodetector when the LED is on is less than 50% of the range of the photodetector. In some examples, the calibration test can determine whether the signal detected by the photodetector is between 20% and 50% of the photodetector signal range. In other examples, the calibration test can determine whether the signal detected by the photodetector is between 25% and 45% of the photodetector signal range. If the calibration check passes, the system can perform proximity checks (1008). If the calibration checks fail, the system can re-calibrate the LED as described above. If the re-calibration fails, the system can determine and/or report that the device is off-wrist (1010). Alternatively, when the calibration checks fail after recalibration (i.e., when recalibration occurs in response to a failed saturation check) has been performed, the system can determine and/or report that the device is off-wrist (1010).

The proximity checks can look at the signal sample and detect whether there is a drop in signal level of a threshold amount for a threshold period of time. For example, a drop in the signal level by more than 25% for 5 seconds can be indicative of a change in proximity between the user's skin and the photodetector and can correspond to a removal of the device from the skin (i.e., a removal event). In other examples the threshold amount of signal level can be set between 15% and 50% of the peak or the running average of recent signal measurements. Additionally, the threshold period of time can be set between 1 and 10 seconds, in some examples. If the proximity check fails (i.e., detects a removal event), the system can determine and/or report that the device is off-wrist (1010). If the proximity checks pass, the system can perform DC checks (1012).

The DC checks can be the same as the DC checks described above. If the DC checks fail, the system can determine and/or report that the device is off-wrist (1010). If the DC checks pass, the system can perform variance checks (1014). The variance checks can be the same as the variance checks described above, though the variance threshold can be different than the variance checks for on-wrist checks. If the variance checks fail, the system can determine and/or report that the device is off-wrist (1010). If the variance checks pass, the system can get the next sample(s) for analysis (1002).

Figure 11:
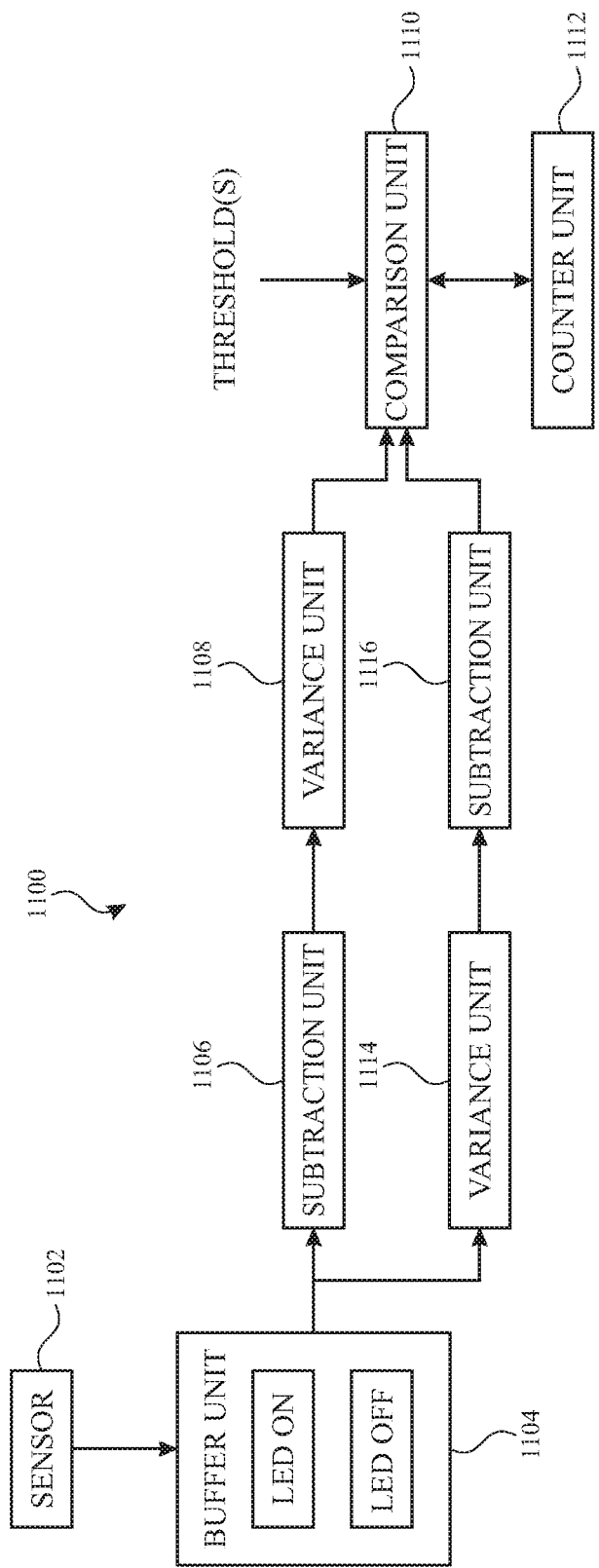
FIG. 11 illustrates a block diagram of functional units that can be contained within or controlled by the processor to perform a variance check algorithm according to examples of the disclosure.

FIG. 11 illustrates a block diagram of functional units that can be contained within or controlled by the processor to perform a variance check algorithm according to examples of the disclosure. The functional units can be implemented as discrete hardware units such as, for example, digital signal processors (DSP), application specific integrated circuits (ASIC), field programmable logic arrays (FPGA), or the like. The functional units can be combined into one or more interconnected devices. Alternatively, the functional units can be implemented in the form of software or firmware (or a combination of the two) configured to operate a programmable processor. Further, the functional units can be a combination of discrete hardware, software and firmware.

Block diagram 1100 includes sensor 1102 for measuring signals that can be used to determine the on-wrist/off-wrist state of the device. For example, the sensor 1102 can include one or more light emitter and light sensor pairs, for example an LED and photodetector pair. The sensor can sample the photodetector at regular intervals, e.g. 5-20 Hz or 50-200 ms. The sensor can also take two samples during each sampling period. One sample can be taken when the LED is on ($LED_{ON}$) and one sample can be taken when the LED is off ($LED_{OFF}$). The $LED_{ON}$ and $LED_{OFF}$ samples can be taken proximate to one another, e.g., within 250 microseconds. Reducing the time between samples can result in better correlation of the samples.

Block diagram 1100 can also include a buffer unit 1104 to store and/or pipeline the $LED_{ON}$ and $LED_{OFF}$ signals received from the buffer unit 1104. In some examples, the buffer unit can separately buffer the $LED_{ON}$ signals and $LED_{OFF}$ signals. Buffer unit 1104 can be one or more first-in first-out (FIFO) buffers configured to receive signals sampled from sensor 1102. Buffer unit 1104 can supply the appropriate quantity of $LED_{ON}$ and $LED_{OFF}$ signals for additional processing. In some examples, the buffer unit 1104 can be controlled by a timing and control unit (not shown).

Block diagram 1100 can also include a first subtraction unit 1106 and a first variance unit 1108. The first subtraction unit 1106 and the first variance unit 1108 can receive the $LED_{ON}$ and $LED_{OFF}$ signals and calculate the variance of the difference between $LED_{ON}$ and $LED_{OFF}$. The output of the first subtraction unit 1106 can be represented by the expression $LED_{ON}$-$LED_{OFF}$, and the output of the first variance unit 1108 can be represented by the expression $VAR(LED_{ON}$-$LED_{OFF})$. Block diagram 1100 can also include a second variance unit 1114 and a second subtraction unit 1116. The second subtraction unit 1116 and the second variance unit 1114 can receive the $LED_{ON}$ and $LED_{OFF}$ signals and calculate the difference between the variance of the $LED_{ON}$ signals and the variance of the $LED_{OFF}$ signals. The output of the second variance unit 1114 can be represented by the expressions $VAR(LED_{ON})$ and $VAR(LED_{OFF})$, and the output of the second subtraction unit 1116 can be represented by the expression $VAR(LED_{ON})$-$VAR(LED_{OFF})$.

Block diagram 1100 can also include a comparison unit 1110. The comparison unit 1110 can receive output from the first variance unit 1108 and from the second subtraction unit 1116 and can receive one or more thresholds. The comparison unit 1110 can compare the output from the first variance unit 1108 (i.e., the first variance calculation, $VAR(LED_{ON}$-$LED_{OFF}))$ and the output from the second subtraction unit 1116 (i.e., the second variance calculation, $VAR(LED_{ON})$-$VAR(LED_{OFF}))$ to the one or more thresholds according to the algorithms described above. Block diagram 1100 can also include the counter unit 1112 that can be incremented, decremented, and/or reset based on comparisons of the first and/or second variance calculations to the one or more thresholds. Comparison unit 1110 can also compare the value of the counter unit 1112 to a counter threshold to determine whether the device is on-wrist or off-wrist.

Figure 12:
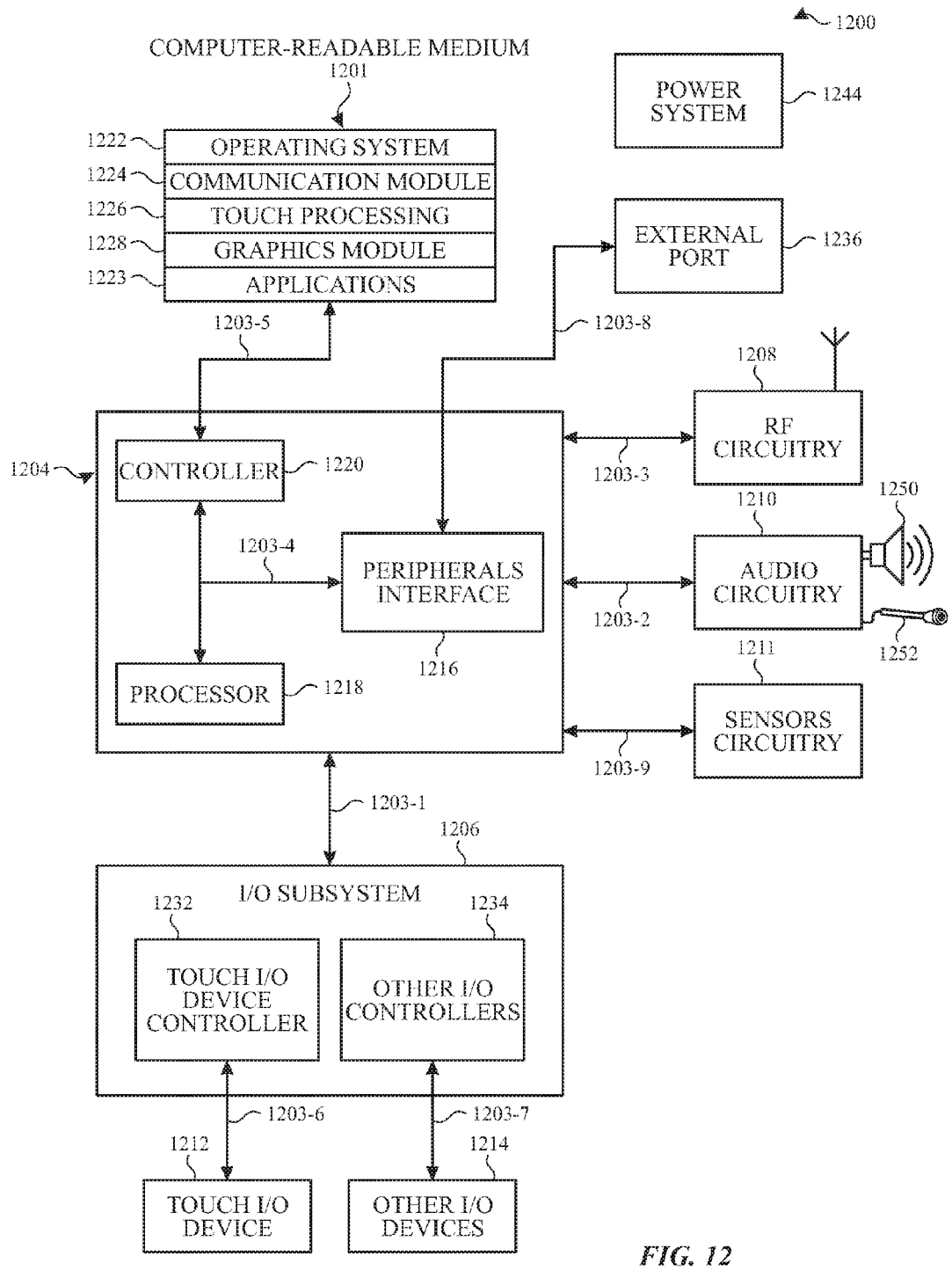
FIG. 12 illustrates a block diagram of an exemplary system architecture that can implement the variance check algorithms according to examples of the disclosure.

A system architecture implementing the variance check algorithms can be included in any portable or non-portable device including but not limited to a wearable device (e.g., smart band, health band, smart watch), a communication device (e.g., mobile phone, smart phone), a multi-media device (e.g., MP3 player, TV, radio), a portable or handheld computer (e.g., tablet, netbook, laptop), a desktop computer, an All-In-One desktop, a peripheral device, or any other system or device adaptable to the inclusion of the system architecture, including combinations of two or more of these types of devices. FIG. 12 illustrates a block diagram of an exemplary system architecture 1200 that can implement the variance check algorithms according to examples of the disclosure. System architecture 1200 can generally include one or more computer-readable media 1201, processing system 1204, I/O subsystem 1206, radio frequency (RF) circuitry 1208, audio circuitry 1210, and sensors circuitry 1211. These components can be coupled by one or more communication buses or signal lines 1203.

It should be understood that the exemplary architecture shown in FIG. 12 can have more or fewer components than shown, or a different configuration of components. The various components shown in FIG. 12 can be implemented in hardware, software, firmware or any combination thereof, including one or more signal processing and/or application specific integrated circuits.

RF circuitry 1208 can be used to send and receive information over a wireless link or network to one or more other devices and includes well-known circuitry for performing this function. RF circuitry 1208 and audio circuitry 1210 can be coupled to processing system 1204 via peripherals interface 1216. Peripherals interface 1216 can include various known components for establishing and maintaining communication between peripherals and processing system 1204. Audio circuitry 1210 can be coupled to audio speaker 1250 and microphone 1252 and can include known circuitry for processing voice signals received from peripherals interface 1216 to enable a user to communicate in real-time with other users. In some examples, audio circuitry 1210 can include a headphone jack (not shown). Sensors circuitry 1211 can be coupled to various sensors including, but not limited to, one or more light emitting diodes (LEDs) or other light emitters, one or more photodiodes or other light sensors, one or more photothermal sensors, a magnetometer, an accelerometer, a gyroscope, a barometer, a compass, a proximity sensor, a camera, an ambient light sensor, a thermometer, a global positioning system (GPS) sensor, and various system sensors which can sense remaining battery life, power consumption, processor speed, CPU load, and the like.

Peripherals interface 1216 can couple the input and output peripherals of the system 1200 to one or more processors 1218 and one or more computer-readable media 1201 via a controller 1220. The one or more processors 1218 communicate with the one or more computer readable media 1201 via the controller 1220. The one more computer-readable media 1201 can be any device or medium that can store code and/or data for use by the one or more processors 1218. In some examples, medium 1201 can be a non-transitory computer-readable storage medium. Medium 1201 can include a memory hierarchy, including but not limited to cache, main memory and secondary memory. The memory hierarchy can, as non-limiting examples, be implemented using any combination of RAM (e.g., SRAM, DRAM, SDRAM), ROM, FLASH, magnetic and/or optical storage devices, such as disk drives, magnetic tape, compact disks (CDs) and digital video discs (DVDs). Medium 1201 can also include a transmission medium for carrying information bearing signals indicative of computer instructions or data (with or without a carrier wave upon which the signals can be modulated). For example, the transmission medium can include a communications network, including but not limited to the Internet (also referred to as the World Wide Web), intranet(s), Local Area Networks (LANs), Wide Local Area Networks (WLANs), Storage Area Networks (SANs), Metropolitan Area Networks (MAN) and the like.

One or more processors 1218 can run various software components stored in medium 1201 to perform various functions for system architecture 1200. In some examples, the software components can include operating system 1222, communication module (or set of instructions) 1224, touch processing module (or set of instructions) 1226, graphics module (or set of instructions) 1228, and one or more applications (or set of instructions) 1223. Each of these modules and above noted applications can correspond to a set of instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules can be combined or otherwise re-arranged in various examples. In some examples, medium 1201 can store a subset of the modules and data structures identified above. Furthermore, medium 1201 can store additional modules and data structures not described above.

Operating system 1222 can include various procedures, sets of instructions, software components and/or drivers for controlling and managing general system tasks (e.g., memory management, storage device control, power management, etc.) and facilitates communication between various hardware and software components.

Communication module 1224 can facilitate communication with other devices over one or more external ports 1236 or via RF circuitry 1208 and can include various software components for handling data received from RF circuitry 1208 and/or external port 1236.

Graphics module 1228 can include various known software components for rendering, animating and displaying graphical objects on a display surface. In examples in which touch I/O device 1212 is a touch sensing display (e.g., touch screen), graphics module 1228 can include components for rendering, displaying, and animating objects on the touch sensing display. The touch I/O device 1212 and/or the other I/O device 1214 can comprise the I/O unit 110 of FIG. 1, and can also incorporate a UI interface permitting a use to select among programming modes of displaying heart rate data when the I/O device is incorporated into a device 112 of FIG. 1. Further, in relation to FIG. 1, the light emitter 102 and light sensor 104 can be part of the I/O device 1214, and the touch screen 120 can correspond to the touch I/O device 1212 of FIG. 12. The I/O unit 110 either integrated within device 112 or via coupling to microphone/speaker 122 can also provide audio outputs as part of the user communications corresponding to audio circuitry 1210 of FIG. 12. Microphone 1252 of FIG. 12 can correspond to the microphone/speaker 122 of FIG. 1.

One or more applications 1223 can include any applications installed on system 1200, including without limitation, a browser, address book, contact list, email, instant messaging, word processing, keyboard emulation, widgets, JAVA-enabled applications, encryption, digital rights management, voice recognition, voice replication, location determination capability (such as that provided by the GPS), a music player, etc.

Touch processing module 1226 can include various software components for performing various tasks associated with touch I/O device 1212 including but not limited to receiving and processing touch input received from touch I/O device 1212 via touch I/O device controller 1232.

I/O subsystem 1206 can be coupled to touch I/O device 1212 and one or more other I/O devices 1214 for controlling or performing various functions. Touch I/O device 1212 can communicate with processing system 1204 via touch I/O device controller 1232, which can include various components for processing user touch input (e.g., scanning hardware). One or more other input controllers 1234 can receive/send electrical signals from/to other I/O devices 1214. Other I/O devices 1214 can include physical buttons, dials, slider switches, sticks, keyboards, touch pads, additional display screens, or any combination thereof.

If embodied as a touch screen, touch I/O device 1212 can display visual output to the user in a GUI. The visual output can include text, graphics, video, and any combination thereof. Some or all of the visual output can correspond to user-interface objects. Touch I/O device 1212 can form a touch sensing surface that accepts touch input from the user. Touch I/O device 1212 and touch screen controller 1232 (along with any associated modules and/or sets of instructions in medium 1201) can detect and track touches or near touches (and any movement or release of the touch) on touch I/O device 1212 and can convert the detected touch input into interaction with graphical objects, such as one or more user-interface objects. In the case in which touch I/O device 1212 is embodied as a touch screen, the user can directly interact with graphical objects that can be displayed on the touch screen. Alternatively, in the case in which touch I/O device 1212 is embodied as a touch device other than a touch screen (e.g., a touch pad), the user can indirectly interact with graphical objects that can be displayed on a separate display screen embodied as I/O device 1214.

Touch I/O device 1212 can be analogous to the multi-touch sensing surface described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1.

In examples for which touch I/O device 1212 is a touch screen, the touch screen can use liquid crystal display (LCD) technology, light emitting polymer display (LPD) technology, organic LED (OLED), or organic electro luminescence (OEL), although other display technologies can be used in other examples.

Feedback can be provided by touch I/O device 1212 based on the user's touch input as well as a state or states of what is being displayed and/or of the computing system. Feedback can be transmitted optically (e.g., light signal or displayed image), mechanically (e.g., haptic feedback, touch feedback, force feedback, or the like), electrically (e.g., electrical stimulation), olfactory, acoustically (e.g., beep or the like), or the like or any combination thereof and in a variable or non-variable manner.

System architecture 1200 can also include power system 1244 for powering the various hardware components and can include a power management system, one or more power sources, a recharging system, a power failure detection circuit, a power converter or inverter, a power status indicator and any other components typically associated with the generation, management and distribution of power in portable devices.

In some examples, peripherals interface 1216, one or more processors 1218, and memory controller 1220 of the processing system 1204 can be implemented on a single chip. In some other examples, they can be implemented on separate chips.

FIGS. 13A-13C illustrate systems in which examples of the disclosure can be implemented. FIG. 13A illustrates an exemplary mobile telephone 1336 that can include a touch screen 1324. FIG. 13B illustrates an exemplary media player 1340 that can include a touch screen 1326. FIG. 13C illustrates an exemplary wearable device 1344 that can include a touch screen 1328 and can be attached to a user using a strap 1346. The systems of FIGS. 13A-13C can implement variance check algorithms described herein.

Therefore, according to the above, some examples of the disclosure are directed to a device. The device can comprise a sensor configured to generate signals and processing circuitry capable of calculating one or more variances based on the generated signals and determining whether the device is secured or not secured to an object based on the one or more variances. The object can be a human wrist. Some examples of the disclosure are directed to a method executed by processing circuitry for predicting a heart rate. The method can comprise receiving signals generated by a sensor, calculating one or more variances based on the generated signals, and determining whether the device is secured or not secured to an object based on the one or more variances. Some examples of the disclosure are directed to non-transitory computer readable storage medium. The computer readable medium can contain instructions that, when executed, perform a method for operating an electronic device. The electronic device can include a processor. The method can comprise receiving signals generated by a sensor, calculating one or more variances based on the generated signals, and determining whether the device is secured or not secured to an object based on the one or more variances.

Some examples of the disclosure are directed to a device. The device can comprise a sensor configured to generate signal samples and processing circuitry. The processing circuitry can be capable of performing one or more variance calculations for each signal sample, predicting a condition of the device based on the one or more variance calculations for each signal sample, and determining that the device is not secured to an object when the predictions of the condition of the device for the signal samples meets a threshold. Additionally or alternatively to one or more of the examples disclosed above, the sensor can comprise a light emitter and a light detector. Additionally or alternatively to one or more of the examples disclosed above, the light emitter can a light emitting diode (e.g., in the infrared range). Additionally or alternatively to one or more of the examples disclosed above, each signal sample can include a first signal generated when the light emitter is on and a second signal generated when the light emitter is off. Additionally or alternatively to one or more of the examples disclosed above, the first signal and second signal of a signal sample can generated within threshold length of time (e.g., 250 microseconds). Additionally or alternatively to one or more of the examples disclosed above, the one or more variance calculations can comprise a first variance calculation of a variance of a difference between the first signal and the second signal of the signal sample. Additionally or alternatively to one or more of the examples disclosed above, predicting the condition of the device based on the one or more variance calculations for each signal sample can comprise, predicting a first condition of the device when the first variance calculation is below a first variance threshold and predicting a second condition of the device when the first variance calculation meets or exceeds the first variance threshold. Additionally or alternatively to one or more of the examples disclosed above, the one or more variance calculations can comprise a second variance calculation of a difference between a variance of the first signal of the signal sample and a variance of the second signal of the signal sample. Additionally or alternatively to one or more of the examples disclosed above, predicting the condition of the device based on the one or more variance calculations for each signal sample can comprise predicting a first condition of the device when the first variance calculation is below a first variance threshold; predicting the first condition of the device when the first variance calculation meets or exceeds the first variance threshold, the first variance calculation is below a second variance threshold, and the second variance calculation is below a third variance threshold; predicting a second condition of the device when the first variance calculation meets or exceeds the first variance threshold and the first variance calculation meets or exceeds the second variance threshold; and predicting the second condition of the device when the first variance calculation meets or exceeds the first variance threshold, the first variance calculation is below the second variance threshold, and the second variance calculation meets or exceeds the third variance threshold. Additionally or alternatively to one or more of the examples disclosed above, the second variance threshold can be greater than the first variance threshold. Additionally or alternatively to one or more of the examples disclosed above, the third variance threshold can be less than the first variance threshold. Additionally or alternatively to one or more of the examples disclosed above, predicting the condition of the device based on the one or more variance calculations for each signal sample can comprise predicting a first condition of the device when the first variance calculation is below a first variance threshold and the first variance calculation is below a third variance threshold; predicting the first condition of the device when the first variance calculation is below the first variance threshold, the first variance calculation meets or exceeds the third variance threshold, and the second variance calculation is below a fourth variance threshold; predicting a second condition of the device when the first variance calculation meets or exceeds the first variance threshold and the first variance calculation meets or exceeds the second variance threshold; and predicting the second condition of the device when the first variance calculation is below the first variance threshold, the first variance calculation meets or exceeds the third variance threshold, and the second variance calculation meets or exceeds the fourth variance threshold. Additionally or alternatively to one or more of the examples disclosed above, the second variance threshold can be greater than the first variance threshold. Additionally or alternatively to one or more of the examples disclosed above, the third variance threshold can be less than the first variance threshold. Additionally or alternatively to one or more of the examples disclosed above, the fourth variance threshold can be less than the third variance threshold. Additionally or alternatively to one or more of the examples disclosed above, the first condition can correspond to a prediction that the device is not secured to the object and the second condition can correspond to a prediction that the device is secured to the object. Additionally or alternatively to one or more of the examples disclosed above, determining that the device is not secured to the object when the predictions of the condition of the device for the signal samples meets the threshold can comprise predicting the first condition for a threshold number of consecutive predictions. Additionally or alternatively to one or more of the examples disclosed above, the object can be human skin. Additionally or alternatively to one or more of the examples disclosed above, the object can be a wrist.

Some examples of the disclosure are directed to a method executed by processing circuitry for determining that a device is not secured to an object. The method can comprise generating a plurality of signal samples, performing one or more variance calculations for each signal sample, predicting a condition of the device based on the one or more variance calculations for each signal sample, and determining that the device is not secured to the object when the predictions of the condition of the device for the signal samples meets a threshold. Additionally or alternatively to one or more of the examples disclosed above, the sensor can comprise a light emitter and a light detector. Additionally or alternatively to one or more of the examples disclosed above, the light emitter can a light emitting diode (e.g., in the infrared range). Additionally or alternatively to one or more of the examples disclosed above, each signal sample can include a first signal generated when the light emitter is on and a second signal generated when the light emitter is off. Additionally or alternatively to one or more of the examples disclosed above, the first signal and second signal of a signal sample can generated within threshold length of time (e.g., 250 microseconds). Additionally or alternatively to one or more of the examples disclosed above, the one or more variance calculations can comprise a first variance calculation of a variance of a difference between the first signal and the second signal of the signal sample. Additionally or alternatively to one or more of the examples disclosed above, predicting the condition of the device based on the one or more variance calculations for each signal sample can comprise, predicting a first condition of the device when the first variance calculation is below a first variance threshold and predicting a second condition of the device when the first variance calculation meets or exceeds the first variance threshold. Additionally or alternatively to one or more of the examples disclosed above, the one or more variance calculations can comprise a second variance calculation of a difference between a variance of the first signal of the signal sample and a variance of the second signal of the signal sample. Additionally or alternatively to one or more of the examples disclosed above, predicting the condition of the device based on the one or more variance calculations for each signal sample can comprise predicting a first condition of the device when the first variance calculation is below a first variance threshold; predicting the first condition of the device when the first variance calculation meets or exceeds the first variance threshold, the first variance calculation is below a second variance threshold, and the second variance calculation is below a third variance threshold; predicting a second condition of the device when the first variance calculation meets or exceeds the first variance threshold and the first variance calculation meets or exceeds the second variance threshold; and predicting the second condition of the device when the first variance calculation meets or exceeds the first variance threshold, the first variance calculation is below the second variance threshold, and the second variance calculation meets or exceeds the third variance threshold. Additionally or alternatively to one or more of the examples disclosed above, the second variance threshold can be greater than the first variance threshold. Additionally or alternatively to one or more of the examples disclosed above, the third variance threshold can be less than the first variance threshold. Additionally or alternatively to one or more of the examples disclosed above, predicting the condition of the device based on the one or more variance calculations for each signal sample can comprise predicting a first condition of the device when the first variance calculation is below a first variance threshold and the first variance calculation is below a third variance threshold; predicting the first condition of the device when the first variance calculation is below the first variance threshold, the first variance calculation meets or exceeds the third variance threshold, and the second variance calculation is below a fourth variance threshold; predicting a second condition of the device when the first variance calculation meets or exceeds the first variance threshold and the first variance calculation meets or exceeds the second variance threshold; and predicting the second condition of the device when the first variance calculation is below the first variance threshold, the first variance calculation meets or exceeds the third variance threshold, and the second variance calculation meets or exceeds the fourth variance threshold. Additionally or alternatively to one or more of the examples disclosed above, the second variance threshold can be greater than the first variance threshold. Additionally or alternatively to one or more of the examples disclosed above, the third variance threshold can be less than the first variance threshold. Additionally or alternatively to one or more of the examples disclosed above, the fourth variance threshold can be less than the third variance threshold. Additionally or alternatively to one or more of the examples disclosed above, the first condition can correspond to a prediction that the device is not secured to the object and the second condition can correspond to a prediction that the device is secured to the object. Additionally or alternatively to one or more of the examples disclosed above, determining that the device is not secured to the object when the predictions of the condition of the device for the signal samples meets the threshold can comprise predicting the first condition for a threshold number of consecutive predictions. Additionally or alternatively to one or more of the examples disclosed above, the object can be human skin. Additionally or alternatively to one or more of the examples disclosed above, the object can be a wrist.

Some examples of the disclosure are directed to non-transitory computer readable storage medium. The computer readable medium can contain instructions that, when executed, perform a method for operating an electronic device. The electronic device can include a processor. The method can comprise generating a plurality of signal samples, performing one or more variance calculations for each signal sample, predicting a condition of the device based on the one or more variance calculations for each signal sample, and determining that the device is not secured to the object when the predictions of the condition of the device for the signal samples meets a threshold. Additionally or alternatively to one or more of the examples disclosed above, the sensor can comprise a light emitter and a light detector. Additionally or alternatively to one or more of the examples disclosed above, the light emitter can a light emitting diode (e.g., in the infrared range). Additionally or alternatively to one or more of the examples disclosed above, each signal sample can include a first signal generated when the light emitter is on and a second signal generated when the light emitter is off. Additionally or alternatively to one or more of the examples disclosed above, the first signal and second signal of a signal sample can generated within threshold length of time (e.g., 250 microseconds). Additionally or alternatively to one or more of the examples disclosed above, the one or more variance calculations can comprise a first variance calculation of a variance of a difference between the first signal and the second signal of the signal sample. Additionally or alternatively to one or more of the examples disclosed above, predicting the condition of the device based on the one or more variance calculations for each signal sample can comprise, predicting a first condition of the device when the first variance calculation is below a first variance threshold and predicting a second condition of the device when the first variance calculation meets or exceeds the first variance threshold. Additionally or alternatively to one or more of the examples disclosed above, the one or more variance calculations can comprise a second variance calculation of a difference between a variance of the first signal of the signal sample and a variance of the second signal of the signal sample. Additionally or alternatively to one or more of the examples disclosed above, predicting the condition of the device based on the one or more variance calculations for each signal sample can comprise predicting a first condition of the device when the first variance calculation is below a first variance threshold; predicting the first condition of the device when the first variance calculation meets or exceeds the first variance threshold, the first variance calculation is below a second variance threshold, and the second variance calculation is below a third variance threshold; predicting a second condition of the device when the first variance calculation meets or exceeds the first variance threshold and the first variance calculation meets or exceeds the second variance threshold; and predicting the second condition of the device when the first variance calculation meets or exceeds the first variance threshold, the first variance calculation is below the second variance threshold, and the second variance calculation meets or exceeds the third variance threshold. Additionally or alternatively to one or more of the examples disclosed above, the second variance threshold can be greater than the first variance threshold. Additionally or alternatively to one or more of the examples disclosed above, the third variance threshold can be less than the first variance threshold. Additionally or alternatively to one or more of the examples disclosed above, predicting the condition of the device based on the one or more variance calculations for each signal sample can comprise predicting a first condition of the device when the first variance calculation is below a first variance threshold and the first variance calculation is below a third variance threshold; predicting the first condition of the device when the first variance calculation is below the first variance threshold, the first variance calculation meets or exceeds the third variance threshold, and the second variance calculation is below a fourth variance threshold; predicting a second condition of the device when the first variance calculation meets or exceeds the first variance threshold and the first variance calculation meets or exceeds the second variance threshold; and predicting the second condition of the device when the first variance calculation is below the first variance threshold, the first variance calculation meets or exceeds the third variance threshold, and the second variance calculation meets or exceeds the fourth variance threshold. Additionally or alternatively to one or more of the examples disclosed above, the second variance threshold can be greater than the first variance threshold. Additionally or alternatively to one or more of the examples disclosed above, the third variance threshold can be less than the first variance threshold. Additionally or alternatively to one or more of the examples disclosed above, the fourth variance threshold can be less than the third variance threshold. Additionally or alternatively to one or more of the examples disclosed above, the first condition can correspond to a prediction that the device is not secured to the object and the second condition can correspond to a prediction that the device is secured to the object. Additionally or alternatively to one or more of the examples disclosed above, determining that the device is not secured to the object when the predictions of the condition of the device for the signal samples meets the threshold can comprise predicting the first condition for a threshold number of consecutive predictions. Additionally or alternatively to one or more of the examples disclosed above, the object can be human skin. Additionally or alternatively to one or more of the examples disclosed above, the object can be a wrist.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A device comprising:
   a sensor comprising a light emitter and a light detector configured to generate signal samples, wherein each signal sample includes a first signal generated when the light emitter is on and a second signal generated when the light emitter is off; and
   processing circuitry coupled to the sensor capable of:
      performing one or more variance calculations for each signal sample, the one or more variance calculations for each signal sample indicative of a first condition or a second condition;
      in accordance with a threshold number of signal samples within a threshold period of time indicating the first condition, determining that the device is not secured to an object; and
      in accordance with fewer than the threshold number of signal samples within the threshold period of time indicating the first condition, determining that the device is secured to the object.

2. The device of claim 1, wherein the one or more variance calculations comprises a first variance calculation of a variance of a difference between the first signal and the second signal of the signal sample.

3. The device of claim 2, wherein the one or more variance calculations for each signal sample indicate the first condition when the first variance calculation is below a first variance threshold and indicate the second condition when the first variance calculation meets or exceeds the first variance threshold.

4. The device of claim 2, wherein the one or more variance calculations comprises a second variance calculation of a difference between a variance of the first signal of the signal sample and a variance of the second signal of the signal sample.

5. The device of claim 4, wherein the one or more variance calculations for each signal sample:
   indicate the first condition when the first variance calculation is below a first variance threshold;
   indicate the first condition when the first variance calculation meets or exceeds the first variance threshold, the first variance calculation is below a second variance threshold, and the second variance calculation is below a third variance threshold;
   indicate the second condition when the first variance calculation meets or exceeds the first variance threshold and the first variance calculation meets or exceeds the second variance threshold; and
   indicate the second condition when the first variance calculation meets or exceeds the first variance threshold, the first variance calculation is below the second variance threshold, and the second variance calculation meets or exceeds the third variance threshold.

6. The device of claim 4, wherein the one or more variance calculations for each signal sample:
   indicate the first condition when the first variance calculation is below a first variance threshold and the first variance calculation is below a third variance threshold;
   indicate the first condition when the first variance calculation is below the first variance threshold, the first variance calculation meets or exceeds the third variance threshold, and the second variance calculation is below a fourth variance threshold;
   indicate the second condition when the first variance calculation meets or exceeds the first variance threshold and the first variance calculation meets or exceeds the second variance threshold; and
   indicate the second condition when the first variance calculation is below the first variance threshold, the first variance calculation meets or exceeds the third variance threshold, and the second variance calculation meets or exceeds the fourth variance threshold.

7. The device of claim 1, wherein the first condition corresponds to a prediction that the device is not secured to the object and wherein the second condition corresponds to a prediction that the device is secured to the object.

8. The device of claim 1, wherein the threshold number of signal samples is equal to a number of signal samples generated within the threshold period of time.

9. A method comprising:
   generating a plurality of signal samples, wherein each signal sample includes a first signal generated when a light emitter is on and a second signal generated when the light emitter is off;
   performing one or more variance calculations for each signal sample, the one or more variance calculations for each signal sample indicative of a first condition or a second condition;
   in accordance with a threshold number of signal samples within a threshold period of time indicating the first condition, determining that a device is not secured to an object; and
   in accordance with fewer than the threshold number of signal samples within the threshold period of time indicating the first condition, determining that the device is secured to the object.

10. The method of claim 9, wherein the one or more variance calculations comprises a first variance calculation of a variance of a difference between the first signal and the second signal of the signal sample.

11. The method of claim 10, wherein the one or more variance calculations for each signal sample indicate the first condition when the first variance calculation is below a first variance threshold and indicate the second condition when the first variance calculation meets or exceeds the first variance threshold.

12. The method of claim 10, wherein the one or more variance calculations comprises a second variance calculation of a difference between a variance of the first signal of the signal sample and a variance of the second signal of the signal sample.

13. A non-transitory computer readable storage medium, the computer readable medium containing instructions that, when executed by an electronic device including a processor and a sensor comprising a light emitter and a light detector, performs a method comprising:
   generating a plurality of signal samples, wherein each signal sample includes a first signal generated when the light emitter is on and a second signal generated when the light emitter is off;

performing one or more variance calculations for each signal sample, the one or more variance calculations for each signal sample indicative of a first condition or a second condition;

in accordance with a threshold number of signal samples within a threshold period of time indicating the first condition, determining that the device is not secured to an object; and in accordance with fewer than the threshold number of signal samples within the threshold period of time indicating the first condition, determining that the device is secured to the object.

14. The non-transitory computer readable storage medium of claim 13, wherein the one or more variance calculations comprises a first variance calculation of a variance of a difference between the first signal and the second signal of the signal sample.

15. The non-transitory computer readable storage medium of claim 14, wherein the one or more variance calculations for each signal sample indicate the first condition when the first variance calculation is below a first variance threshold and indicate the second condition when the first variance calculation meets or exceeds the first variance threshold.

16. The non-transitory computer readable storage medium of claim 14, wherein the one or more variance calculations comprises a second variance calculation of a difference between a variance of the first signal of the signal sample and a variance of the second signal of the signal sample.

17. The non-transitory computer readable storage medium of claim 16, wherein the one or more variance calculations for each signal sample:

indicate the first condition when the first variance calculation is below a first variance threshold;

indicate the first condition when the first variance calculation meets or exceeds the first variance threshold, the first variance calculation is below a second variance threshold, and the second variance calculation is below a third variance threshold;

indicate the second condition when the first variance calculation meets or exceeds the first variance threshold and the first variance calculation meets or exceeds the second variance threshold; and indicate the second condition when the first variance calculation meets or exceeds the first variance threshold, the first variance calculation is below the second variance threshold, and the second variance calculation meets or exceeds the third variance threshold.

18. The non-transitory computer readable storage medium of claim 16, wherein the one or more variance calculations for each signal sample:

indicate the first condition when the first variance calculation is below a first variance threshold and the first variance calculation is below a third variance threshold;

indicate the first condition when the first variance calculation is below the first variance threshold, the first variance calculation meets or exceeds the third variance threshold, and the second variance calculation is below a fourth variance threshold;

indicate the second condition when the first variance calculation meets or exceeds the first variance threshold and the first variance calculation meets or exceeds the second variance threshold; and indicate the second condition when the first variance calculation is below the first variance threshold, the first variance calculation meets or exceeds the third variance threshold, and the second variance calculation meets or exceeds the fourth variance threshold.

19. The non-transitory computer readable storage medium of claim 13, wherein the first condition corresponds to a prediction that the device is not secured to the object and wherein the second condition corresponds to a prediction that the device is secured to the object.

20. The non-transitory computer readable storage medium of claim 13, wherein the threshold number of signal samples is equal to a number of signal samples generated within the threshold period of time.

* * * * *